United States Patent
Baldwin

Patent Number: 5,295,478
Date of Patent: Mar. 22, 1994

[54] MOUTH-TO-MASK RESUSCITATOR

[76] Inventor: Gene R. Baldwin, 324 N. Gardiner Ave., Rockford, Ill. 61107

[21] Appl. No.: 18,194

[22] Filed: Feb. 16, 1993

[51] Int. Cl.⁵ .................... A61M 16/20; A61M 16/00
[52] U.S. Cl. .................... 128/203.11; 128/202.28; 128/202.29; 137/855; 137/512.4
[58] Field of Search ............. 128/203.11, 202.27, 128/202.28, 202.29; 137/855, 512.4, 515.5, 515

[56] References Cited

U.S. PATENT DOCUMENTS

| | | | |
|---|---|---|---|
| 3,460,558 | 8/1969 | Johannisson | 137/102 |
| 3,812,878 | 5/1974 | Bird et al. | 137/855 |
| 3,830,632 | 8/1974 | Guzay | 128/205.28 |
| 4,229,832 | 10/1980 | Dickson, Sr. | 128/201.28 |
| 4,449,525 | 5/1984 | White et al. | 128/203.1 |
| 4,926,855 | 5/1990 | Hellquist et al. | 128/207.12 |
| 5,146,914 | 9/1992 | Sturrock | 128/203.11 |

Primary Examiner—Edgar S. Burr
Assistant Examiner—Katharina W. Trautman
Attorney, Agent, or Firm—Brady, O'Boyle & Gates

[57] ABSTRACT

A mouth-to-mask resuscitator which can be carried in a person's pocket consisting of an oronasal mask and a check valve which is inserted into the mask and allows a person to administer artificial ventilation to fill the victim's lung with air and to allow the victim to exhale air through an exit in the valve assembly away from the person administering the resuscitation. The mask is foldable into itself to form a cavity for storing the check valve which has inspiratory and exhalation air flow back pressures meeting ISO standards.

6 Claims, 1 Drawing Sheet

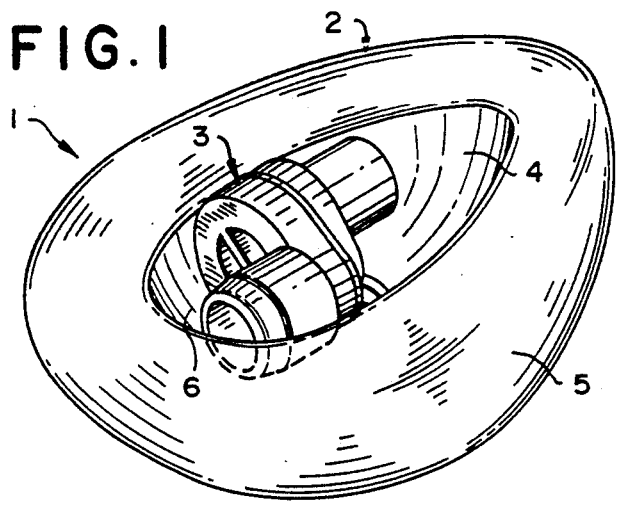
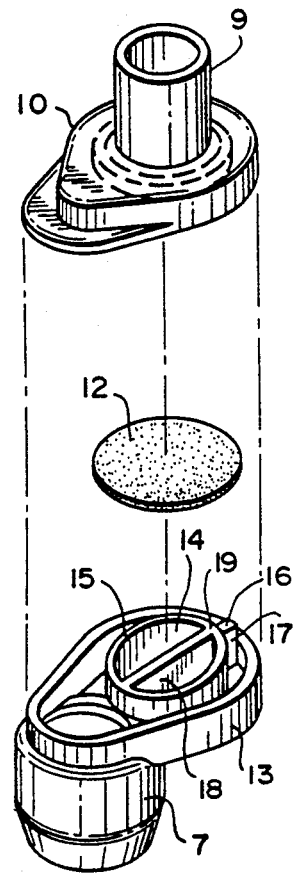
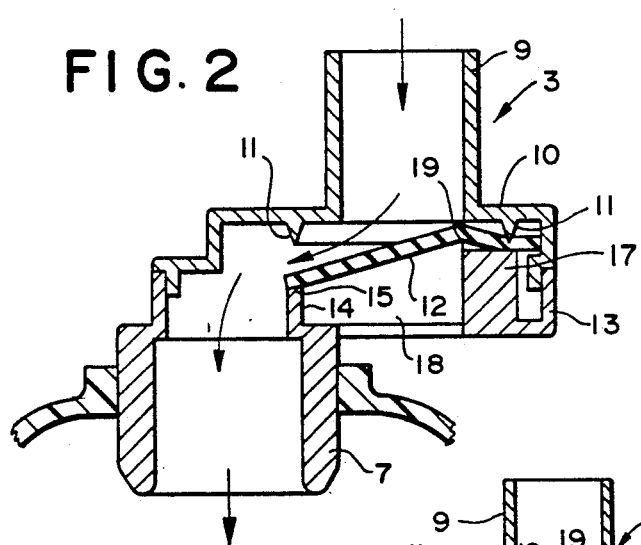
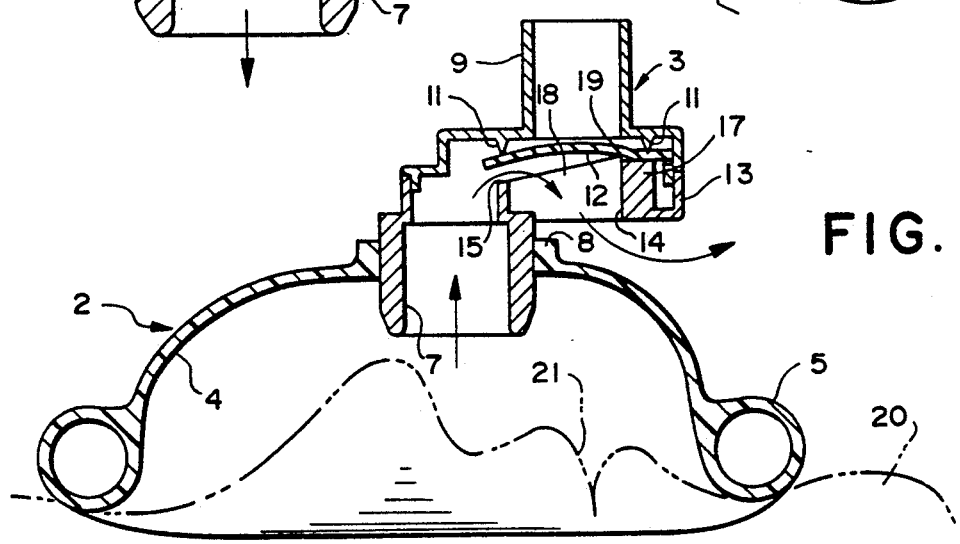

MOUTH-TO-MASK RESUSCITATOR

BACKGROUND OF THE INVENTION

To revive a non-breathing person, mouth-to-mouth resuscitation is often employed in an emergency situation. In order to reduce the risk of the transmission of communicable diseases during the resuscitation process, the mouth-to-mask resuscitator of the present invention has been devised.

SUMMARY OF THE INVENTION

The mouth-to-mask resuscitator of the present invention comprises, essentially, an oronasal mask constructed and arranged to seal around the mouth and nose of a non-breathing person, and a non-rebreathing or check valve assembly insertable into the mask, whereby a person can administer artificial ventilation by blowing into the valve and mask assembly to fill the non-breathing person's or victim's lungs with air, and to allow the victim to exhale air through an exit in the valve away from the person.

The oronasal mask is foldable, and the removable check valve is placed within the folded mask for storage.

BRIEF DESCRIPTION OF THE DRAWINGS

FIG. 1 is a perspective view of the oronasal mask in the folded position with the check valve placed therein for storage;

FIG. 2 is a fragmentary, sectional view showing the valve mounted in the operative position on the oronasal mask and showing the flow of air from the person administering the artificial ventilation;

FIG. 3 is a sectional side elevational view of the resuscitator placed on the mouth and nose of the victim and showing the flow of exhaled air from the patient; and FIG. 4 is an exploded view of the valve employed with the mask.

DESCRIPTION OF THE PREFERRED EMBODIMENT

Referring to the drawing and more particularly to FIG. 1, the mouth-to-mask resuscitator 1 of the present invention comprises an oronasal mask 2, and a non-rebreathing or check valve 3 insertable into the mask 2. The mask 2 and valve 3 are shown in FIG. 1 in the stored position, and which can be placed in a suitable container, not shown, and carried in one's pocket. To accomplish this, the mask 2 includes a dome portion 4 made of flexible material integral with a hollow, resilient, annular base portion 5. The flexible dome portion 4 can be folded into itself to form a cavity 6 for receiving the valve 3 laying sideways therein. To mount the valve 3 in the operative position on the mask 2, as shown in FIG. 3, the dome portion 4 is pushed outwardly to extend above the base portion 5 and a tubular portion 7 of the valve 3 is inserted into an opening in the mask 2 and frictionally held therein by a peripheral wall portion 8 extending around the opening.

The valve 3 comprises an offset tubular inlet 9 having a stepped base portion 10 formed with a depending, annular, knife edge 11 providing a seat for a resilient valve disc 12. The base portion 10 of the inlet tube 9 is integrally connected to a housing 13 having a cross-sectional configuration corresponding to the base portion 10. The tubular portion 7 is offset on the housing 10 in a manner similar to the tubular inlet 9 on the base portion 10, and a through bore 14 is provided in the housing 13 communicating the interior of the housing 13 with the atmosphere. The top peripheral edge 15 of the bore 14 is inclined and provides a seat for the resilient valve disc 12 which is secured at one point along its periphery between the base portion 10 and housing 13 by the depending knife edge 11 pressing the peripheral portion of the disc 12 against the top surface 16 of a vertically extending post 17 integral with the outer wall surface of the bore 14. Because the diameter of the disc valve 12 is close to the diameter of the peripheral edge 15, a diametrically extending rib 18 is provided in the bore 14 to prevent the pressure of exhaled air of the operator from pushing the disc valve 12 into the bore 14. The portion of the peripheral edge 15 and the outer portion 19 of the rib 18 adjacent the post 17 is higher than the top surface 16 of the post 17, to thereby form a hinge for biasing the disc valve 12 against the annular knife edge 11.

In use, the mask 2 and associated valve 3 are placed on the victim, as shown in FIG. 3, so that the annular base portion 5 of the mask seals the resuscitator around nose 20 and mouth 21 of the victim, and the tubular portion 7 of the valve is inserted into the opening in the mask. The operator or person administering the artificial ventilation blows through tubular inlet 9 to move the valve disc 12 from the knife edge 11, as shown in FIG. 2, to the peripheral edge 15, to thereby establish communication between inlet 9 and tubular portion 7, whereby air is forced into the victim's lungs. When the operator stops blowing, the disc valve 12 returns to the original position against the knife edge 11, as shown in FIG. 3, whereby the victim's exhaled air flows through the tubular portion 7 and bore 14 to the atmosphere.

It is imperative that a resuscitator be designed to allow the least amount of air flow resistance both for inspiratory flow, FIG. 2, and exhalation, FIG. 3. The maximum resistance set by ISO draft standard ISO/DIS 8382 is 5 cm/$H_2O$ for exhalation and 5 cm/$H_2O$ for inspiratory at 50 L/min. flow. It will be appreciated by those skilled in the art that these standards are achieved by the construction and arrangement of the mouth-to-mask resuscitator of the present invention. To accomplish this, the valve inlet 9, tubular portion 7, and bore 14 are designed to have the largest openings possible, while keeping the overall size of the valve to a minimum, and the resilient disc 12 is dimensioned to the extent of the peripheral edge 15 to allow for the least amount of air flow resistance into and out of the valve.

It is to be understood that the form of the invention herewith shown and described is to be taken as a preferred example of the same, and that various changes in the shape, size and arrangement of parts may be resorted to, without departing from the spirit of the invention or scope of the subjoined claims.

I claim:

1. A mouth-to-mask resuscitator comprising an oronasal mask having a dome portion made of flexible material, a hollow, resilient, annular base portion integral with said dome portion, an opening in said dome portion, a check valve assembly having a tubular portion, said tubular portion being insertable into said opening, a peripheral wall portion extending around said opening for frictionally holding said tubular portion and thus said check valve assembly on said dome portion, said flexible dome portion being foldable into itself to form a cavity for receiving the check valve assembly, whereby the mouth-to-mask resuscitator is transformed to a storage position adapted to be carried in a person's pocket; the check valve assembly comprising, a base portion and a tubular inlet integral with said base portion, a depending annular knife edge formed on said base portion, a housing, said tubular portion being integral with said housing, the base portion of said tubular inlet being integrally connected to said housing, a through bore provided in said housing communicating the interior of the housing with the atmosphere, one end of said bore having a peripheral edge, a resilient valve disc positioned between the base portion of said tubular inlet and said housing, a post having a top surface integral with the exterior surface of said bore, said depending knife edge pressing the peripheral portion of said disc against the top surface of said post, thereby securing the valve disc at one place within its periphery between the base portion of the tubular inlet and the housing, whereby the knife edge on the base portion of said tubular inlet and the peripheral edge on said one end of the bore provide seats for the valve disc, and a diametrically extending rib mounted within said bore to prevent the pressure of exhaled air from pushing the disc valve into said bore, one end of said rib being positioned adjacent said post, said one end of said rib being higher than the top surface of the post, to thereby form a hinge for biasing the disc valve against the annular knife edge.

2. A check valve assembly for use in a mouth-to-mask resuscitator comprising, a base portion and a tubular inlet integral with said base portion, a depending annular knife edge formed on said base portion, a housing, a tubular portion being integral with said housing, the base portion of said tubular inlet being integrally connected to said housing, a through bore provided in said housing communicating the interior of the housing with the atmosphere, one end of said bore having a peripheral edge, a resilient valve disc positioned between the base portion of said tubular inlet and said housing, a post having a top surface integral with the exterior surface of said bore, said depending knife edge pressing the peripheral portion of said disc against the top surface of said post to thereby secure the valve disc at one place within its periphery between the base portion of the tubular inlet and the housing, whereby the knife edge on the base portion of said tubular inlet and the peripheral edge on said one end of the bore provide seats for the valve disc, and a diametrically extending rib mounted within the bore to prevent the disc valve from being pushed into said bore, one end portion of said rib being adjacent said post, said one end portion being higher than the top surface of the post, to thereby form a hinge for biasing the disc valve against the annular knife edge.

3. A mouth-to-mask resuscitator comprising an oronasal mask having a dome portion made of flexible material, a hollow, resilient, annular base portion integral with said dome portion, an opening in said dome portion, a check valve assembly having a tubular portion, said tubular portion being insertable into said opening, a peripheral wall portion extending around said opening for frictionally holding said tubular portion and thus said check valve assembly on said dome portion, said flexible dome portion being foldable into itself to form a cavity for receiving the check valve assembly, whereby the mouth-to-mask resuscitator is transformed to a storage position adapted to be carried in a person's pocket; the check valve assembly comprising, a base portion and a tubular inlet integral with said base portion, a depending annular edge formed on said base portion, a housing, said tubular portion being integral with said housing, the base portion of said tubular inlet being integrally connected to said housing, a through bore provided in said housing communicating the interior of the housing with the atmosphere, one end of said bore having a peripheral edge, a resilient valve disc positioned between the base portion of said tubular inlet and said housing, a post having a top surface integral with the exterior surface of said bore, said depending annular edge pressing the peripheral portion of said disc against the top surface of said post, thereby securing the valve disc at one place within its periphery between the base portion of the tubular inlet and the housing, whereby the depending annular edge on the base portion of said tubular inlet and the peripheral edge on said one end of the bore provide seats for the valve disc, the portion of the peripheral edge adjacent said post being higher than the top surface of the post, to thereby form a hinge for biasing the disc valve against the depending annular edge.

4. A mouth-to-mask resuscitator according to claim 3, wherein a diametrically extending rib is mounted within the bore to prevent the pressure of exhaled air from pushing the disc valve into said bore.

5. A check valve assembly for use in a mouth-to-mask resuscitator comprising, a base portion and a tubular inlet integral with said base portion, a depending annular edge formed on said base portion, a housing, a tubular portion being integral with said housing, the base portion of said tubular inlet being integrally connected to said housing, a through bore provided in said housing communicating the interior of the housing with the atmosphere, one end of said bore having a peripheral edge, a resilient valve disc positioned between the base portion of said tubular inlet and said housing, a post having a top surface integral with the exterior surface of said bore, said depending annular edge pressing the peripheral portion of said disc against the top surface of said post to thereby secure the valve disc at one place within its periphery between the base portion of the tubular inlet and the housing, whereby the annular edge on the base portion of said tubular inlet and the peripheral edge on said one end of the bore provide seats for the valve disc, the portion of the peripheral edge adjacent said post being higher than the top surface of the post, to thereby form a hinge for biasing the disc valve against the depending annular edge.

6. A check valve assembly according to claim 5, wherein a diametrically extending rib is mounted within the bore to prevent the pressure of exhaled air from pushing the disc valve into said bore.

* * * * *